(12) United States Patent
Fish et al.

(10) Patent No.: US 11,348,666 B2
(45) Date of Patent: *May 31, 2022

(54) SYSTEM AND METHOD TO ENABLE A KIOSK TO AGGREGATE WIRELESS DEVICES AND REPORT HEALTH INFORMATION TO A MOBILE CONSUMER DEVICE

(71) Applicant: 19Labs, Inc., San Mateo, CA (US)

(72) Inventors: Ram Fish, Menlo Park, CA (US); Jerry Horel, Brentwood Bay (CA)

(73) Assignee: 19Labs, Inc., San Mateo, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 16/582,848

(22) Filed: Sep. 25, 2019

(65) Prior Publication Data

US 2020/0082919 A1 Mar. 12, 2020

Related U.S. Application Data

(63) Continuation-in-part of application No. 16/264,152, filed on Jan. 31, 2019, now Pat. No. 11,283,615.
(Continued)

(51) Int. Cl.
*G16H 10/20* (2018.01)
*H04W 4/80* (2018.01)
(Continued)

(52) U.S. Cl.
CPC .............. *G16H 10/20* (2018.01); *G06F 21/35* (2013.01); *G16H 80/00* (2018.01); *H04W 4/021* (2013.01); *H04W 4/80* (2018.02)

(58) Field of Classification Search
CPC . H04L 9/3234; H04L 9/3226; H04L 2209/80; H04L 2209/76; H04L 2209/805;
(Continued)

(56) References Cited

U.S. PATENT DOCUMENTS 8,661,249 B2 2/2014 Guarraci
9,047,648 B1 6/2015 Lekutai
(Continued)

FOREIGN PATENT DOCUMENTS

WO 2017/070638 A1 4/2017

*Primary Examiner* — Mohammad W Reza
(74) *Attorney, Agent, or Firm* — Inventive Law Inc.; Jim H. Salter

(57) ABSTRACT

A system and method to enable a kiosk to aggregate wireless devices and report health information to a mobile consumer device is disclosed. A particular embodiment is implemented for: configuring a kiosk to detect the presence of a mobile device in the proximity of the kiosk; configuring the mobile device to detect the presence of kiosk in the proximity of the mobile device; prompting a user of the mobile device to perform a login operation on the mobile device upon detection of the kiosk in the proximity of the mobile device; verifying the authentication of the user with the mobile device as a result of the login operation on the mobile device; and establishing a wireless data connection between a medical diagnostic device connected with the kiosk and the mobile device to wirelessly transfer the user's health data from the kiosk to the mobile device.

20 Claims, 6 Drawing Sheets

Related U.S. Application Data

(60) Provisional application No. 62/736,225, filed on Sep. 25, 2018, provisional application No. 62/728,848, filed on Sep. 9, 2018.

(51) Int. Cl.
  *H04W 4/021* (2018.01)
  *G06F 21/35* (2013.01)
  *G16H 80/00* (2018.01)

(58) Field of Classification Search
  CPC .............. H04L 2209/56; G06Q 20/18; G06Q 20/3224; G06Q 20/4014; G06Q 20/40; G06Q 20/40145; H04W 12/0471; H04W 4/80; H04W 12/63
  See application file for complete search history.

(56) References Cited

U.S. PATENT DOCUMENTS

| | | |
|---|---|---|
| 9,100,392 B2 | 8/2015 | Hubner |
| 9,414,776 B2 | 8/2016 | Sillay |
| 9,438,587 B2 | 9/2016 | Hardy |
| 9,443,073 B2 | 9/2016 | Oberheide |
| 9,455,988 B2 | 9/2016 | Oberheide |
| 9,553,872 B2 | 1/2017 | Tippett |
| 9,819,684 B2 | 11/2017 | Cernoch |
| 9,825,765 B2 | 11/2017 | Oberheide |
| 9,930,060 B2 | 3/2018 | Oberheide |
| 9,979,719 B2 | 5/2018 | Oberheide |
| 10,055,732 B1 | 8/2018 | Hecht |
| 10,078,425 B2 | 9/2018 | Ullrich |
| 2006/0106646 A1 | 5/2006 | Squilla |
| 2011/0191123 A1 | 8/2011 | Buzynski |
| 2011/0288874 A1* | 11/2011 | Hinkamp ............... G16H 10/60 705/1.1 |
| 2012/0059911 A1 | 3/2012 | Randhawa |
| 2012/0197664 A1* | 8/2012 | Maresh ................. G16H 10/60 705/3 |
| 2014/0330579 A1* | 11/2014 | Cashman .............. E04H 1/1222 705/2 |
| 2015/0089607 A1 | 3/2015 | Hubner |
| 2015/0213661 A1* | 7/2015 | Robertson .......... G07C 9/00571 340/5.61 |
| 2015/0242601 A1 | 8/2015 | Griffiths |
| 2017/0141920 A1 | 5/2017 | Herder, III |
| 2018/0096547 A1 | 4/2018 | Robertson |
| 2018/0130548 A1* | 5/2018 | Fisher ................... G16H 10/65 |

\* cited by examiner

US 11,348,666 B2

SYSTEM AND METHOD TO ENABLE A KIOSK TO AGGREGATE WIRELESS DEVICES AND REPORT HEALTH INFORMATION TO A MOBILE CONSUMER DEVICE

PRIORITY PATENT APPLICATIONS

This is a non-provisional patent application drawing priority from U.S. provisional patent application Ser. No. 62/736,225; filed Sep. 25, 2018. This is also a continuation-in-part (CIP) patent application drawing priority from U.S. non-provisional patent application Ser. No. 16/264,152; filed Jan. 31, 2019; which is a non-provisional patent application drawing priority from U.S. provisional patent application Ser. No. 62/728,848; filed Sep. 9, 2018. This present non-provisional CIP patent application draws priority from the referenced patent applications. The entire disclosure of the referenced patent applications is considered part of the disclosure of the present application and is hereby incorporated by reference herein in its entirety.

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2017-2019 19Labs, Inc., All Rights Reserved.

TECHNICAL FIELD

This patent application relates to computer-implemented software systems, mobile devices, kiosk systems, according to various embodiments, and more specifically to a system and method to enable a kiosk to aggregate wireless devices and report health information to a mobile consumer device.

BACKGROUND

In many cases, it is convenient for people to use kiosks to perform various transactions. For example, automatic teller machines (ATMs) enable a user to withdraw cash from a user bank account without interacting with a human teller. Airports use kiosks to enable ticket purchase or check-in without human interaction. The healthcare industry can also benefit from the use of kiosks for the capture, processing, retention, and presentation of routine user/patient medical data, such as blood pressure, heartrate, temperature, blood glucose level, and the like, again without the need for human interaction. Healthcare kiosks with different diagnostic devices can be used to collect patient data and send the patient data to the network cloud. However, many consumers are keeping this patient data and other information on their mobile devices (e.g., phones) rather than or in addition to storing the data in the cloud. Healthcare diagnostic devices are costly; so, it doesn't make sense to require these diagnostic devices to be at each consumer home.

SUMMARY

In various example embodiments described herein, a system and method to enable a kiosk to aggregate wireless devices and report health information to a mobile consumer device is disclosed. In the various example embodiments described herein, a computer-implemented tool or software application (app) as part of a healthcare kiosk system is described to automate and improve the interaction of a user at the kiosk by use of a mobile device. As described in more detail below, a computer or computing system on which the described embodiments can be implemented can include, personal communication devices (e.g., cellular telephones, smartphones, or other wireless devices), personal digital assistants (PDAs), portable computing devices, laptops, tablet computers, network computers, consumer electronic devices, wearable computing devices, or any other type of computing, data processing, communication, networking, or electronic system. In various example embodiments described herein, a user health data transfer system allows a user to easily and quickly interact with a kiosk by use of a mobile device. The various example embodiments described herein enable the user to access and use a public healthcare kiosk with a mobile device to perform various medical diagnostic tests of the user's health using multiple diagnostic devices (e.g., blood pressure device, weight/scale, glucose level detector, etc.) provided by the kiosk. The user/patient information generated or provided by the multiple diagnostic devices of the kiosk can be wirelessly transferred from the kiosk to the user's mobile device and/or the network cloud. As a result, the various example embodiments described herein enable efficient upload of user/patient information from the healthcare kiosk into a user's mobile device and cloud service in single process. This process improves and expands the usage of healthcare kiosks and provides benefits for users of the system. Further details of the various example embodiments are described below.

BRIEF DESCRIPTION OF THE DRAWINGS

The various embodiments are illustrated by way of example, and not by way of limitation, in the figures of the accompanying drawings in which.

DETAILED DESCRIPTION

In the following description, for purposes of explanation, numerous specific details are set forth in order to provide a thorough understanding of the various embodiments. It will be evident, however, to one of ordinary skill in the art that the various embodiments may be practiced without these specific details.

In various example embodiments described herein, a system and method to enable a kiosk to aggregate wireless devices and report health information to a mobile consumer device is disclosed. In the various example embodiments described herein, a computer-implemented tool or software application (app) as part of a healthcare kiosk system is described to automate and improve the interaction of a user at the kiosk by use of a mobile device. As described in more detail below, a computer or computing system on which the described embodiments can be implemented can include, personal communication devices (e.g., cellular telephones, smartphones, or other wireless devices), personal digital assistants (PDAs), portable computing devices, laptops, tablet computers, network computers, consumer electronic devices, wearable computing devices, or any other type of computing, data processing, communication, networking, or electronic system. In various example embodiments described herein, a user health data transfer system allows a user to easily and quickly interact with a kiosk by use of a mobile device. The various example embodiments described herein enable the user to access and use a public healthcare kiosk with a mobile device to perform various medical diagnostic tests of the user's health using multiple diagnostic devices (e.g., blood pressure device, weight/scale, glucose level detector, etc.) provided by the kiosk. The user/patient information generated or provided by the multiple diagnostic devices of the kiosk can be wirelessly transferred from the kiosk to the user's mobile device and/or the network cloud. As a result, the various example embodiments described herein enable efficient upload of user/patient information from the healthcare kiosk into a user's mobile device and cloud service in single process. This process improves and expands the usage of healthcare kiosks and provides benefits for users of the system. Further details of the various example embodiments are described below.

Figure 1:
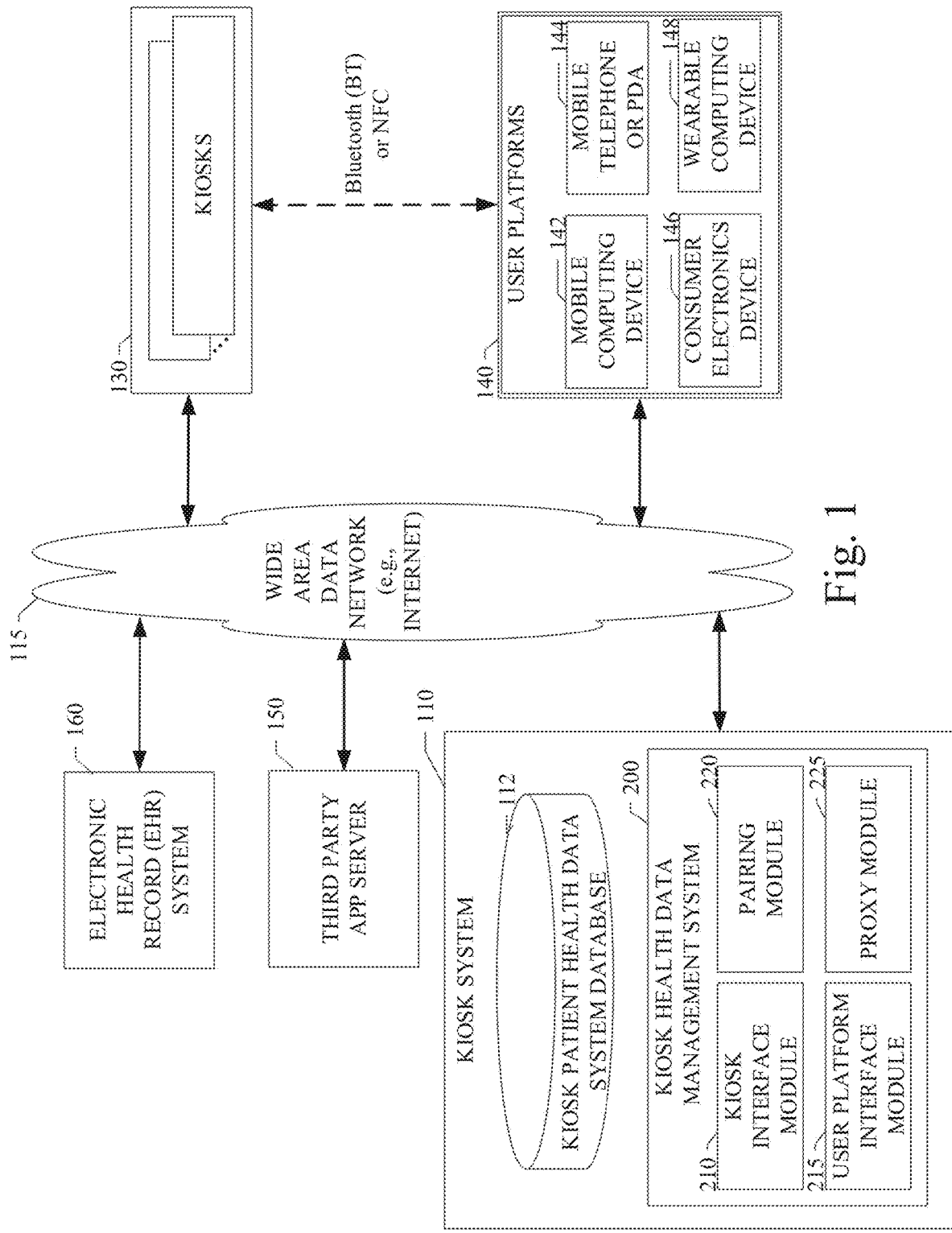
FIG. 1 illustrates an example embodiment of a networked system in which various embodiments may operate.

FIG. 1, in an example embodiment, illustrates a system and method to enable a kiosk to aggregate wireless devices and report health information to a mobile consumer device of a user platform. In various example embodiments, an application or service, typically provided by or operating on a host site (e.g., a server) 110, is provided to simplify and facilitate the use of the kiosk health data management system 200 of an example embodiment. In a particular embodiment, the kiosk health data management system 200 can be hosted by the host site 110 for a networked user at a user platform 140 and a kiosk 130 of a plurality of available kiosks. As used herein, the term 'kiosk' denotes a small structure, typically in a public area, that is used for accepting input from a user and providing information or displaying results to a user. The kiosk often incorporates a data processor and an interactive display screen or screens. The details of the kiosk health data management system 200 and the kiosks for an example embodiment are provided below.

Referring again to FIG. 1, the kiosk health data management system 200 can be in network communication with a plurality of kiosks 130. The kiosks 130 can include user input devices, sensor devices, medical devices, health diagnostic devices, communication devices, and/or network resources at which a user/consumer can provide input and receive a presentation of information from the kiosk 130. The kiosk 130 can also provide a portal for the user/consumer to access other third party sites, such as other third party application sites 150 or electronic health record (EHR) sites 160. The kiosk health data management system 200 can be configured to provide data communications and health data transfer services for user/consumers at the user platforms 140 serving as networked platforms for user/consumers to interact with a kiosk 130 and subsequently provide or obtain user/consumer information, medical and health information, medical diagnostic information, advisory information, and the like in a digital or computer-readable form via the network 115. The kiosks 130 can include user input devices, sensor devices, medical devices, health diagnostic devices, communication devices, and/or network resources configured to serve as networked platforms for user/consumers to provide or obtain consumer information including, consumer profile information, consumer medical/health information, advisory information, consumer product interests, or other consumer-related information. The kiosk health data management system 200 can be configured to facilitate the collection, transfer, and presentation of this consumer health information at a kiosk 130 and/or a user device at a user platform 140 in a digital or computer-readable form via the network 115 and/or via a local wireless data transfer (e.g., Bluetooth™ (BT) and/or Near-field Communication (NFC)). The kiosk health data management system 200 can also be in network data communication with a plurality of other information sites, such as third party application sites 150, electronic health record (EHR) sites 160, and the like. These types of third party application sites 150 and electronic health record (EHR) sites 160 are well known to those of ordinary skill in the art.

One or more of the kiosks 130 can be provided by one or more third party providers operating at various locations in a network ecosystem. It will be apparent to those of ordinary skill in the art that kiosks 130 can include or be any of a variety of networked third party information collectors/providers or on-line vendors or merchants as described in more detail below. In a particular embodiment, a resource list maintained at the host site 110 can be used as a summary or list of all kiosks 130, which users at user platforms 140 or the host site 110 may visit/access and from which users or the host site 110 can obtain or present consumer health data. The host site 110, the plurality of kiosks 130, the user platforms 140, third party application sites 150, and electronic health record (EHR) sites 160 may communicate and transfer data and information in the data network ecosystem shown in FIG. 1 via a wide area data network (e.g., the Internet) 115. As described in more detail below, the kiosks 130 and the user platforms 140 may also directly communicate wirelessly while in close proximity using conventional wireless data communication technologies, such as Bluetooth™ (BT) and/or Near-field Communication (NFC). BT and NFC are different sets of communication protocols that enable two electronic devices, one or both of which is usually a portable or mobile device such as a smartphone, to establish communication by bringing the devices within close proximity.

Network 115 is configured to couple one computing device with another computing device. Network 115 may be enabled to employ any form of computer readable media for communicating information from one electronic device to another. Network 115 can include the Internet or a local area network (LAN), wide area networks (WANs), direct connections, such as through a universal serial bus (USB) port, other forms of computer-readable media, or any combination thereof. On an interconnected set of LANs, including those based on differing architectures and protocols, a router and/or gateway device acts as a link between LANs, enabling messages to be sent between computing devices. Also, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communication links known to those of ordinary skill in the art. Furthermore, remote computers and other related electronic devices can be remotely connected to either LANs or WANs via a wireless link, WiFi, Bluetooth™, satellite, or modem and temporary telephone link.

Network 115 may further include any of a variety of wireless sub-networks that may further overlay stand-alone ad-hoc networks, and the like, to provide an infrastructure-oriented connection. Such sub-networks may include mesh networks, Wireless LAN (WLAN) networks, cellular networks, and the like. Network 115 may also include an autonomous system of terminals, gateways, routers, and the like connected by wireless radio links or wireless transceivers. These connectors may be configured to move freely and randomly and organize themselves arbitrarily, such that the topology of network 115 may change rapidly and arbitrarily.

Network 115 may further employ a plurality of access technologies including 2nd (2G), 2.5, $3^{rd}$ (3G), $4^{th}$ (4G) $5^{th}$ (5G) generation radio access for cellular systems, WLAN, Wireless Router (WR) mesh, and the like. Access technologies such as 2G, 3G, 4G, 5G, and future access networks may enable wide area coverage for mobile devices, such as one or more of client devices 140, with various degrees of mobility. For example, network 115 may enable a radio connection through a radio network access such as Global System for Mobile communication (GSM), General Packet Radio Services (GPRS), Enhanced Data GSM Environment (EDGE), Wideband Code Division Multiple Access (WCDMA), CDMA2000, and the like. Network 115 may also be constructed for use with various other wired and wireless communication protocols, including TCP/IP, UDP, SIP, SMS, RTP, WAP, CDMA, TDMA, EDGE, UMTS, GPRS, GSM, UWB, WiFi, WiMax, IEEE 802.11x, and the like. In essence, network 115 may include virtually any wired and/or wireless communication mechanisms by which information may travel between one computing device and another computing device, network, and the like. In one embodiment, network 115 may include a LAN that is configured behind a firewall (not shown), within a business data center, for example.

Kiosks 130 may include data processing components to collect or provide any of a variety of network transportable digital data. The network transportable digital data can be transported in any of a family of file formats and associated mechanisms usable to enable a host site 110 and a user platform 140 to provide or receive user/consumer health data over the network 115 and/or via a local wireless data transfer (e.g., BT and/or NFC). In example embodiments, the file format can be any conventional or proprietary data interchange format supported by the various embodiments described herein. Moreover, the kiosks 130 or user platforms 140 may provide or use a variety of different data sets or computational modules.

In a particular embodiment, a user platform 140 with one or more client devices enables an authorized user, as authorized by the kiosk health data management system 200 via the host 110 and network 115, to access data provided or collected by a kiosk 130. Client devices of user platform 140 may include virtually any computing device that is configured to send and receive information over a network, such as network 115 and/or a local wireless data network (e.g., BT and/or NFC). Such client devices of user platform 140 may include portable or mobile computing devices 142, such as handheld computers, laptops, tablet computers, integrated devices combining one or more of the preceding devices, and the like. The client devices 142 may also include other computing devices, such as personal computers, multiprocessor systems, microprocessor-based or programmable electronics, network PC's, and the like. Such client devices of user platform 140 may also include portable or mobile communication devices 144, such as cellular telephones, smartphones, smartwatches, camera phones, display pagers, radio frequency (RF) devices, infrared (IR) devices, global positioning devices (GPS), Personal Digital Assistants (PDAs), or the like. The client devices of user platform 140 may also include other data processing devices, such as consumer electronic (CE) devices 146 and/or wearable computing devices 148, which are known to those of ordinary skill in the art. As such, the client devices of user platform 140 may range widely in terms of capabilities and features. A web-enabled client device may include a browser application enabled to receive and to send wireless application protocol messages (WAP), and/or wired application messages, and the like. In one embodiment, the browser application is enabled to employ HyperText Markup Language (HTML), Dynamic HTML, Handheld Device Markup Language (HDML), Wireless Markup Language (WML), WMLScript, JavaScript™, EXtensible HTML (xHTML), Compact HTML (CHTML), and the like, to display and/or send digital information. In other embodiments, mobile devices of user platform 140 can be configured with applications (apps) with which the functionality described herein can be implemented and/or supported.

The client devices of user platform 140 may also include at least one client application that is configured to provide or receive consumer health data and/or control data from another computing device via a wired or wireless network transmission. The client application may include a capability to provide and receive textual data, graphical data, video data, audio data, and the like. Moreover, client devices of user platform 140 may be further configured to communicate and/or receive a message, such as through a Short Message Service (SMS), direct messaging (e.g., Twitter™), email, Multimedia Message Service (MMS), instant messaging (IM), internet relay chat (IRC), mIRC, Jabber, Enhanced Messaging Service (EMS), text messaging, Smart Messaging, Over the Air (OTA) messaging, or the like, between another computing device, and the like.

Referring again to FIG. 1, the kiosk health data management system 200 for an example embodiment is shown to include a kiosk patient health data system database 112. The database 112 can be used to retain a variety of information data sets including, but not limited to, user/consumer information, patient health information, medical diagnostic information, kiosk configuration information, user platform configuration information, public/private keys, user/consumer analytics, and the like. It will be apparent to those of ordinary skill in the art that the kiosk patient health data system database 112 can be locally resident at the host site 110 or remotely located at other server locations or stored in network cloud storage.

Referring again to FIG. 1, host site 110 of an example embodiment is shown to include the kiosk health data management system 200. In an example embodiment, kiosk health data management system 200 can include a kiosk interface module 210, a user platform interface module 215, a pairing module 220, and a proxy nodule 225. Each of these modules can be implemented as software components executing within an executable environment of kiosk health data management system 200 operating on host site 110. Each of these modules of an example embodiment is described in more detail below in connection with the figures provided herein.

Referring still to FIG. 1, the kiosk health data management system 200 can include a kiosk interface module 210 and user platform interface module 215. The kiosk interface module 210 can facilitate communication and the transfer of data between a user at a kiosk 130 and the host site 110. The user platform interface module 215 can facilitate communication and the transfer of data between a user of a mobile device at a user platform 140 and the host site 110. The pairing module 220 can facilitate and authorize the pairing of and communication between a particular kiosk 130 and a particular user mobile device of a user platform 140. The proxy module 225 can facilitate the communication between a particular kiosk 130 or a particular user mobile device of a user platform 140 with a third party server 150 or an EHR system 160. The kiosk interface module 210, the user platform interface module 215, the pairing module 220, and the proxy module 225 can be configured to perform the processing as described in more detail below. The kiosk interface module 210 and the user platform interface module 215 can be resident at the host site 110 or partially resident on the user platforms 140. The kiosk health data management system 200 can be configured to provide user authentication and data communications for the kiosks 130 and the mobile devices of user platforms 140 to enable the networked usage, transfer, uploading or downloading of information, requests, images, documents, and related data to facilitate the gathering, processing, validation, and presentation of consumer information related to a user/consumer transaction at a kiosk 130. The components and processes for the gathering, processing, validation, and presentation of consumer health information related to a user/consumer transaction at a kiosk 130 as embodied in the kiosk health data management system 200, the kiosk 130, and the mobile device of a user platform 140 are described in more detail below.

Figure 2:
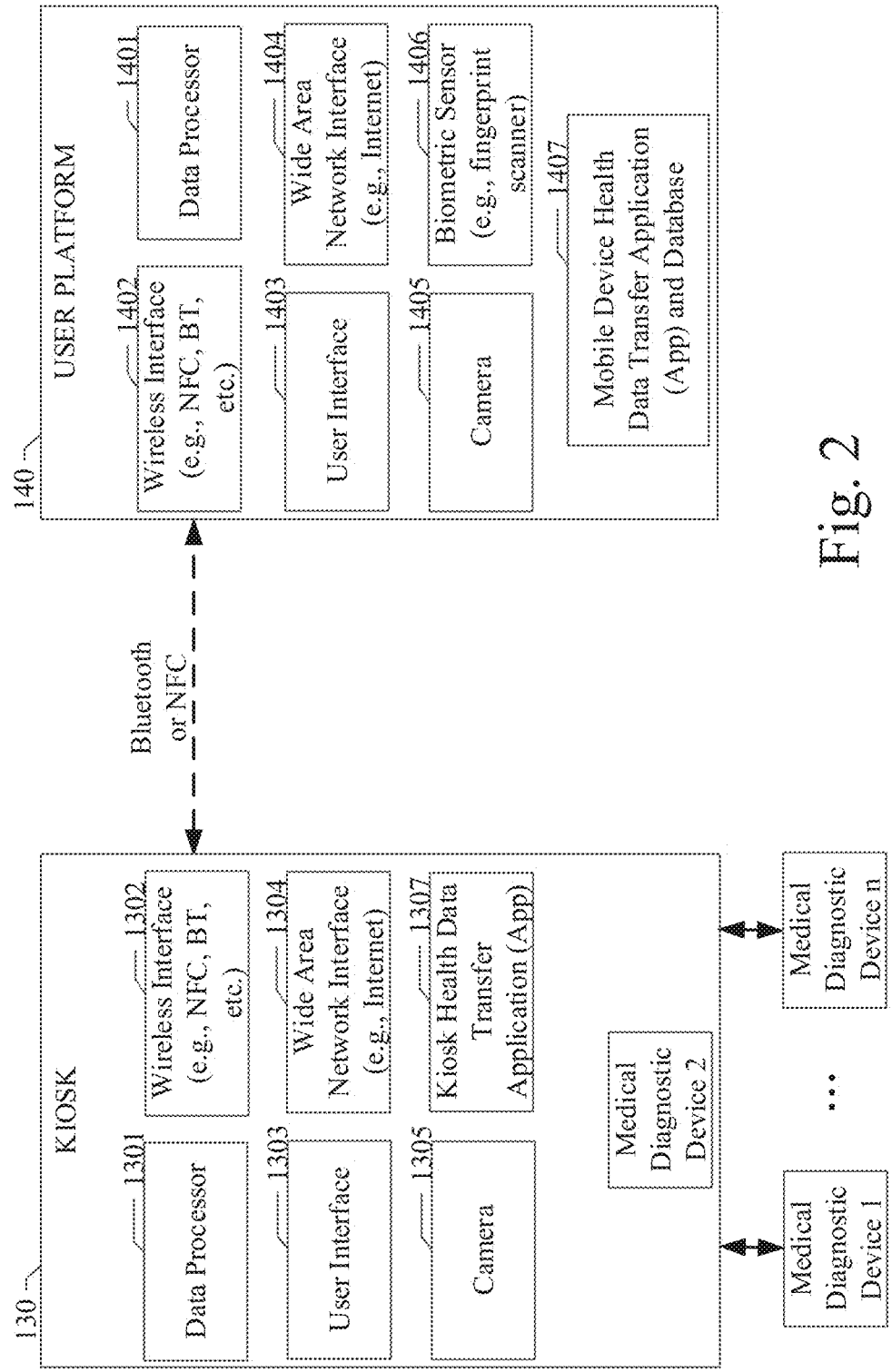
FIG. 2 illustrates the basic components of the kiosk and the user platform of an example embodiment.

FIG. 2 illustrates the basic components of the kiosks 130 and the user platforms 140 of an example embodiment. In an example embodiment, the kiosks 130 can include a data processor 1301, a wireless data network interface 1302, a user interface 1303, a wide area data network interface 1304, a camera or other image capture device 1305, and a kiosk health data transfer application (app) 1307. The data processor 1301 can be any standard data processor, microprocessor, or computing system, or data processing system. The wireless data network interface 1302 can include standard data interfaces and protocols for wirelessly exchanging data via NFC or Bluetooth™. Other conventional wireless communication protocol, such as IEEE 802.11x may also be used in alternative embodiments. The user interface 1303 can include the hardware and software elements to present information to a user of the kiosk 130 and the elements to receive user input. The user interface 1303 can include conventional display devices, input buttons or softkeys, mouse or trackball devices, gesture recognition devices, visual or audio input devices, voice recognition devices, or the like. The wide area data network interface 1304 can include standard data interfaces and protocols for exchanging data via a wide area network, such as the Internet, local area networks (LANs), or other network ecosystems. The camera or other image capture device 1305 can include standard video cameras, still image cameras, specialized imaging cameras, or the like. The kiosk health data transfer application (app) 1307 comprises a set of data processor 1301 instructions that are locally resident and executed on the kiosk 130. The kiosk health data transfer app 1307 can be downloaded to the kiosk 130 via the wide area data network interface 1304 and stored in a memory device of the kiosk 130. Alternatively, the kiosk health data transfer app 1307 can be installed on the kiosk 130 as firmware or logic devices. The kiosk health data transfer app 1307 can be executed by the data processor 1301. The details of the functionality implemented by the kiosk health data transfer app 1307 are described below. It will be apparent to those of ordinary skill in the art in view of the disclosure herein that other features, hardware, and software elements can be provided in or by a particular kiosk 130. Kiosk 130 can also include or be interfaced with medical diagnostic devices, such as blood pressure sensing devices, heart rate sensing devices, weight measuring devices (scales), oxygen saturation level measuring devices, glucose level measuring devices, and the like. By their application, kiosks 130 tend to vary widely in the features offered for the particular application. For example, some kiosks 130 can include credit card readers, printers, or the like. Nevertheless, the data transfer techniques disclosed herein can be used across a broad range of specially configured kiosk systems.

In an example embodiment, the user platforms 140 (e.g., a user mobile device) can include a data processor 1401, a wireless data network interface 1402, a user interface 1403, a wide area data network interface 1404, a camera or other image capture device 1405, a biometric sensor input device 1406, and a mobile device health data transfer application (app) 1407 locally resident and executed on the mobile device 140. The data processor 1401 can be any standard data processor, microprocessor, or computing system, or data processing system. The wireless data network interface 1402 can include standard data interfaces and protocols for wirelessly exchanging data via NFC or Bluetooth™. Other conventional wireless communication protocol, such as IEEE 802.11x may also be used in alternative embodiments. The user interface 1403 can include the hardware and software elements to present information to a user of the user platform 140 and the elements to receive user input. The user interface 1403 can include conventional display devices, input buttons or softkeys, mouse or trackball devices, gesture recognition devices, visual or audio input devices, voice recognition devices, or the like. The wide area data network interface 1404 can include standard data interfaces and protocols for exchanging data via a wide area network, such as the Internet, local area networks (LANs), or other network ecosystems. The camera or other image capture device 1405 can include standard video cameras, still image cameras, specialized imaging cameras, or the like. The biometric sensor input device 1406 can include fingerprint scanners, retinal scanners, face or voice recognition devices, or other devices configured to capture biometric data from a user. The mobile device health data transfer application (app) 1407 can be a set of data processor 1401 instructions that are locally resident and executed on the mobile device 140. The mobile device health data transfer app 1407 can be downloaded via the wide area data network interface 1404 and stored in a memory device of the mobile device 140. The mobile device health data transfer app 1407 can be executed by the data processor 1401. It will be apparent to those of ordinary skill in the art in view of the disclosure herein that other features, hardware, and software elements can be provided in or by a particular user platform 140. In the various embodiments described herein, a mobile device, such as a smartphone, can be used as the user platform 140.

Nevertheless, the wireless data transfer of health information as disclosed herein can be used across a broad range of commercially available user platform systems.

Kiosks 130 are used in a variety of locations and applications. Often, these locations are in public venues. However, because users typically share private and relevant personalized information, kiosks 130 require the user to authenticate with the kiosk 130 prior to sharing confidential information. In most cases, the kiosk 130 requires a user to enter a user identifier (userid) and a password or passcode. However, the entry of the userid and/or the password can be problematic as users typically forget their userid and/or passwords. Many users store their userids and/or passwords on their mobile devices, such as a smartphones, which enable the user to not have to remember the userids or passwords. In some cases, userids or other user credentials are connected with biometric authentication devices and protocols that are available on many standard mobile devices, such as the iPhone™. As a result, the user cannot produce their userid and/or passwords, cannot authenticate with the kiosk 130 and thus, cannot use the kiosk 130.

To solve this problem with kiosk 130 authentication, the example embodiments disclosed herein allow the user to easily log into the kiosk 130 using their mobile device, such as a smartphone. In this manner, the authentication devices and protocols that are available on many standard mobile devices can be easily leveraged and used for logging into a kiosk 130 without having to remember a userid or password. Additionally, the biometric authentication devices and protocols and credential wallets that are available on many standard mobile devices can also be easily leveraged and used for logging into a kiosk 130, while maintaining a high level of security.

In the various example embodiments described herein, a three stage user authentication protocol is used as summarized below. Prior to the operational use of the kiosk 130 as described herein, the kiosk health data transfer app 1307 can be downloaded or otherwise installed on the kiosk 130. Similarly, the mobile device health data transfer app 1407 can be downloaded or otherwise installed on the mobile device 140. In an example embodiment, the three stage user authentication protocol to authenticate a user at a kiosk 130 via a user mobile device 140 can be implemented as follows:

Stage 1. Pairing—The kiosk 130 is configured to detect the presence of a user mobile device 140 in the proximity of the kiosk 130. The user mobile device 140 can also be configured to detect the presence of a kiosk 130 in the proximity of the mobile device 140. The detection of the user mobile device 140 and/or kiosk 130 can be performed using the wireless data network interface 1302 of the kiosk 130 and the wireless data network interface 1402 of the mobile device 140. In an alternative embodiment, the user can also be prompted to enter a passcode or PIN from the kiosk 130 (via user interface 1303) to provide a level of user authentication. In some cases, based on the security level of the pairing or the application used, the confirmation might be automatic. In this case, after the Stage 1 pairing, the mobile device 140 can pass a secure token to the kiosk 130, and/or report the pairing to the kiosk health data management system server 110. The passcode or PIN can be presented to the user on the kiosk 130 or the mobile device 140, requiring entry on the opposite device.

Stage 2. User Authentication—Upon detection of a user mobile device 140 in the proximity of the kiosk 130, the kiosk health data transfer app 1307 can prompt a user of the mobile device 140 to perform a login operation on their mobile device 140. Similarly, upon the detection of a kiosk 130 in the proximity of the user mobile device 140, the mobile device health data transfer app 1407 can prompt the user of the mobile device 140 to perform a login operation on their mobile device 140. The login operation performed by the user on their mobile device 140 can be the standard authentication method used for the particular type of mobile device 140. The standard authentication method for some mobile devices 140 is the entry of a password or passcode. The standard authentication method for other mobile devices 140 is the use of a biometric sensor, such as a fingerprint scanner or facial recognition system. In either case, the example embodiments described herein can leverage the standard authentication methods for mobile devices 140 to verify authentication of the user with the mobile device 140 detected in proximity of the kiosk 130. The mobile device health data transfer app 1407 can validate the authentication of the user with the mobile device 140.

Stage 3. Key Transfer—Once the authentication of the user with the mobile device 140 detected in proximity of the kiosk 130 is validated, the mobile device health data transfer app 1407 can transfer unique kiosk session keys from the mobile device 140 to the kiosk 130 in proximity of the mobile device 140. The transfer of the unique kiosk session keys from the user mobile device 140 to the kiosk 130 can be performed using a secure protocol of the wireless data network interface 1302 of the kiosk 130 and the wireless data network interface 1402 of the mobile device 140. Once the kiosk 130 receives the unique kiosk session keys from the mobile device 140 via the secure wireless protocol, the kiosk health data transfer app 1307 can use the unique kiosk session keys to validate the authentication of the user with the mobile device 140 and with the kiosk 130 in proximity of the mobile device 140. As a result, the kiosk health data transfer app 1307 can use the unique kiosk session keys to authenticate and enable the user with the mobile device 140 to initiate a session on the kiosk 130 without requiring the user to perform a separate authentication process on the kiosk 130. In another example embodiment, the unique kiosk session keys can be sent to the kiosk 130 via a NFC bump process. The NFC bump process is a well-known for direct device data transfer. In another example embodiment, the unique kiosk session keys can be sent to the kiosk 130 via a proxy server. The proxy module 225 of the kiosk health data management system 200 and the wide area data network interface 1304 of the kiosk 130 can be used for this process. In an example embodiment, the unique kiosk session keys can be represented as an encrypted token comprising a combination of the user identifier and a session identifier. Once the authentication of the user with the mobile device 140 detected in proximity of the kiosk 130 is validated and the unique kiosk session keys are sent from the mobile device 140 to the kiosk 130 in proximity of the mobile device 140, the user has been authorized at both the mobile device 140 and the proximate kiosk 130. At this point, the user can also be authorized to access a third party application system server 150 or electronic health record (EHR) sites 160 as described above. The unique kiosk session keys associated with the particular user and corresponding mobile device 140 can be used to authenticate the user with the third party application system server 150 or electronic health record (EHR) sites 160. The unique kiosk session keys can be sent directly to the third party application system server 150 or electronic health record (EHR) sites 160 for authenticated login or sent via a proxy server. As such, the mobile device 140 authentication processes as described herein can be used to integrate mobile devices 140, kiosks 130, and third party application system server 150 or electronic health record (EHR) sites 160.

Figure 3:
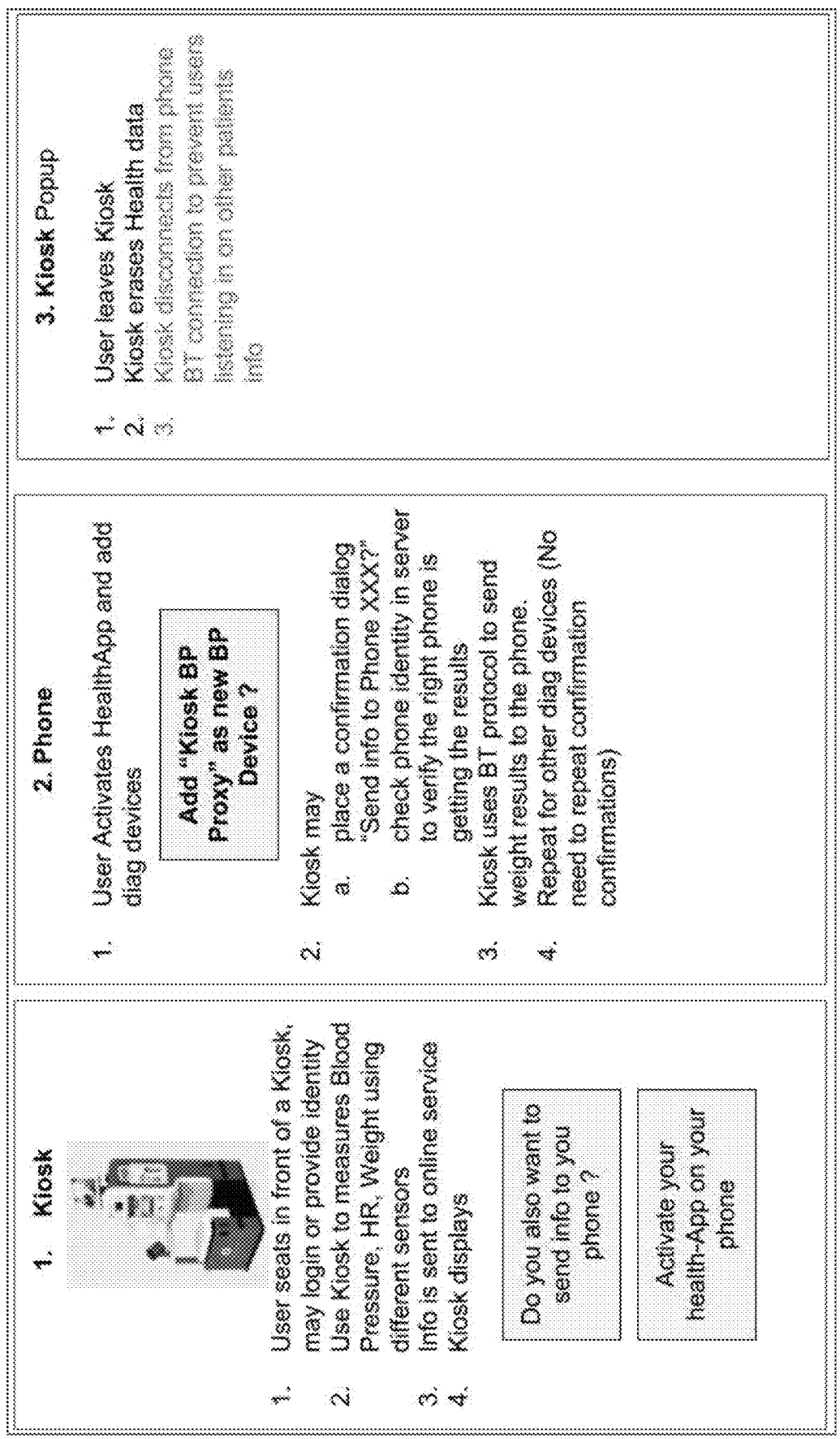
FIG. 3 illustrates a user interface example of a user interaction at a kiosk from a mobile device of a user platform according to an example embodiment of a method as described herein.

FIG. 3 illustrates a user interface example of a user interaction at a kiosk from a mobile device of a user platform according to an example embodiment of a method as described herein. As an initial task not shown in FIG. 3, a user of a mobile device 140 installs the mobile device health data transfer app 1407 on their mobile device. Referring still to FIG. 3, upon completion of the installation of the mobile device health data transfer app 1407 on the user's mobile device 140, the user can position themselves in front of a particular kiosk 130. The kiosk health data transfer app 1307 can use the user interface 1303 to prompt a kiosk 130 user to use their mobile device health data transfer app 1407 to perform a login operation on their mobile device 140. The user prompt can be a message presented on the display device of the kiosk 130 (e.g., user interface 1303). Similarly, the mobile device health data transfer app 1407 can use the user interface 1403 to query the user of the mobile device 140 to determine if the user wants to perform a login operation for a proximate kiosk 130. The kiosk 130 can begin to scan the proximity of the kiosk 130 for a responding mobile device 140. The wireless data network interface 1302 of the kiosk 130 and the wireless data network interface 1402 of the mobile device 140 can be used for this process. If the kiosk 130 detects a user mobile device 140 in the proximity of the kiosk 130, the kiosk health data transfer app 1307 can receive the mobile device 140 identifier of the proximate mobile device from the mobile device 140. The kiosk health data transfer app 1307 can send a list of the mobile device 140 identifiers of the proximate mobile devices to the kiosk health data management system 200 and the pairing module 220 therein. The mobile device health data transfer app 1407 can send to the pairing module 220 a mobile device 140 identifier (e.g., a MAC address or IP address), a user identifier, a mobile device 140 geographical location (e.g., GPS coordinates or location description), a mobile device 140 configuration, and/or the like. The mobile device health data transfer app 1407 can also send to the pairing module 220 a public key corresponding to the particular mobile device 140. The pairing module 220 can compare the list of proximate mobile device 140 identifiers received from the kiosk 130 and the kiosk 130 geographical locations with the mobile device 140 identifier and mobile device 140 geographical location corresponding to the proximate mobile device 140. In particular, the pairing module 220 can determine if a particular mobile device 140 detected near a particular kiosk 130 is compatible with and approved for interaction with the kiosk 130 based on the mobile device 140 identifier, the kiosk 130 identifier, the kiosk 130 geographical location, the mobile device 140 geographical location, the kiosk 130 type or model code, the kiosk 130 configuration, the user identifier and related user information, the kiosk 130 type or model codes with which the mobile device 140 can be paired, the mobile device 140 configuration, and/or the like. Based on this determination, the pairing module 220 can determine if the proximate mobile device 140 is compatible with and approved for interaction with the kiosk 130. If the pairing module 220 approves the interaction between the proximate mobile device 140 and the kiosk 130, the kiosk health data transfer app 1307 and the user interface 1303 can confirm the pairing of the proximate mobile device 140 and the kiosk 130 and prompt the user of the proximate mobile device 140 to perform a login operation on their mobile device 140. The mobile device health data transfer app 1407 and the user interface 1403 can also prompt the user of the proximate mobile device 140 to perform a login operation on their mobile device 140 and/or use a kiosk authentication procedure on the proximate mobile device 140 with kiosk 130 information to authenticate with the nearby kiosk 130. Optionally, the user can be prompted to enter a passcode or PIN for a second level of authentication. As a result, the example real-time pairing operation is complete.

Referring still to FIG. 3, upon completion of the pairing of the mobile device 140 with the kiosk 130 and the authentication and login of the user, the user can use the diagnostic devices of the kiosk 130 to gather medical data related to the health metrics of the user. For example, the user can employ medical diagnostic devices of the kiosk 130, such as blood pressure sensing devices, heart rate sensing devices, weight measuring devices (scales), oxygen level measuring devices, glucose level measuring devices, and the like. The user's health data gathered or produced by the medical diagnostic devices of the kiosk 130 can be initially retained by the kiosk 130. Subsequently, the user's health data can be securely transferred from the kiosk 130 to the kiosk server system 110 via network 115. Additionally, as shown in FIG. 3, the user interface of the kiosk 130 can query the user to determine if the user may want to wirelessly transfer the user's health data from the kiosk 130 to the user's mobile device 140. If the user chooses to perform this wireless data transfer, the user is prompted by the kiosk 130 user interface to activate the mobile device health data transfer app 1407 on the user's mobile device 140.

Referring still to FIG. 3, upon activation of the mobile device health data transfer app 1407 on the user's mobile device 140, the user interface on the user's mobile device 140 can prompt the user to specify or select a particular medical diagnostic device (e.g., blood pressure—BP device, etc.) of kiosk 130 from which the user wishes to obtain health data. Once the user selects a particular medical diagnostic device, the kiosk 130 can add a proxy for the selected medical diagnostic device of the kiosk 130 to serve as a new medical diagnostic device proxy, which can be used by the mobile device 140 to wirelessly transfer the health data from the selected medical diagnostic device to the mobile device 140. In a similar fashion, the kiosk 130 can add a proxy for any of the medical diagnostic devices integrated with, connected to, or configured for communication with the kiosk 130. As such, the kiosk 130 can aggregate the collection of connected medical diagnostic devices into a single wireless communication channel for communicating a user's health data to a mobile device 140. In this manner, the kiosk can communicate with and gather different sets of health data from a plurality of medical diagnostic devices. Then, the kiosk 130 can add a proxy for a particular medical diagnostic device of the kiosk 130, thereby 'pretending' to act as the particular medical diagnostic device when communicating with the mobile device 140. The kiosk 130 can also use the proxy for a particular medical diagnostic device of the kiosk 130 to transfer the user's health data to the network cloud. Thus, the kiosk 130 can use the proxy for a particular medical diagnostic device to separately send the user's health data to the user's mobile device 140 and/or the network cloud. This allows the user to take single sets of health measurements on a particular medical diagnostic device and direct the transfer of the health data to multiple destinations.

Once the new proxy for the medical diagnostic device is added, the wireless interface of the user's mobile device 140 can detect the presence of the medical diagnostic device of the kiosk 130. When the presence of the medical diagnostic device is detected, the user's mobile device 140 can initiate a wireless data transfer connection between the medical diagnostic device of the kiosk 130 and the user's mobile device 140. The mobile device health data transfer app 1407 can be used for this process. Once the wireless data transfer connection between the medical diagnostic device of the kiosk 130 and the user's mobile device 140 is established, the user's health data can be wirelessly transferred from the medical diagnostic device of the kiosk 130 to the user's mobile device 140. As described above, any of several wireless protocols (e.g., BT, NFC, etc.) can be used for this wireless data transfer. The user interface of the kiosk 130 can also prompt the user to perform any needed actions to facilitate the wireless data transfer. For example, the user can be prompted to authenticate the user's identity or the identity of the user's mobile device. The user can repeat the process to obtain the user's health data from any of the medical diagnostic devices attached or interfaced with the kiosk 130. The user can also be offered the option to transfer the user's health data to network cloud storage. The user interface of the kiosk 130 or mobile device 140 can be used for this purpose.

Referring still to FIG. 3, the user can wirelessly transfer the user's health data from any of the kiosk 130 medical diagnostic devices to the user's mobile device or network cloud storage. When the user has completed the desired data transfers, the user can simply leave the proximity of the kiosk. The departure of the user's mobile device from the proximity of the kiosk 130 will cause the wireless data connection to disconnect. Upon detection of the wireless data disconnection, the kiosk 130 can logout the user and erase the user's health data from the kiosk 130. The wireless data connection with the user's mobile device can also be terminated to ensure the security of the user's data. Thus, the user can conveniently and securely establish a wireless data connection between a kiosk 130 medical diagnostic device and the user's mobile device to wirelessly transfer the user's health data from the kiosk 130 to the user's mobile device 140 and/or network cloud storage.

Figure 4:
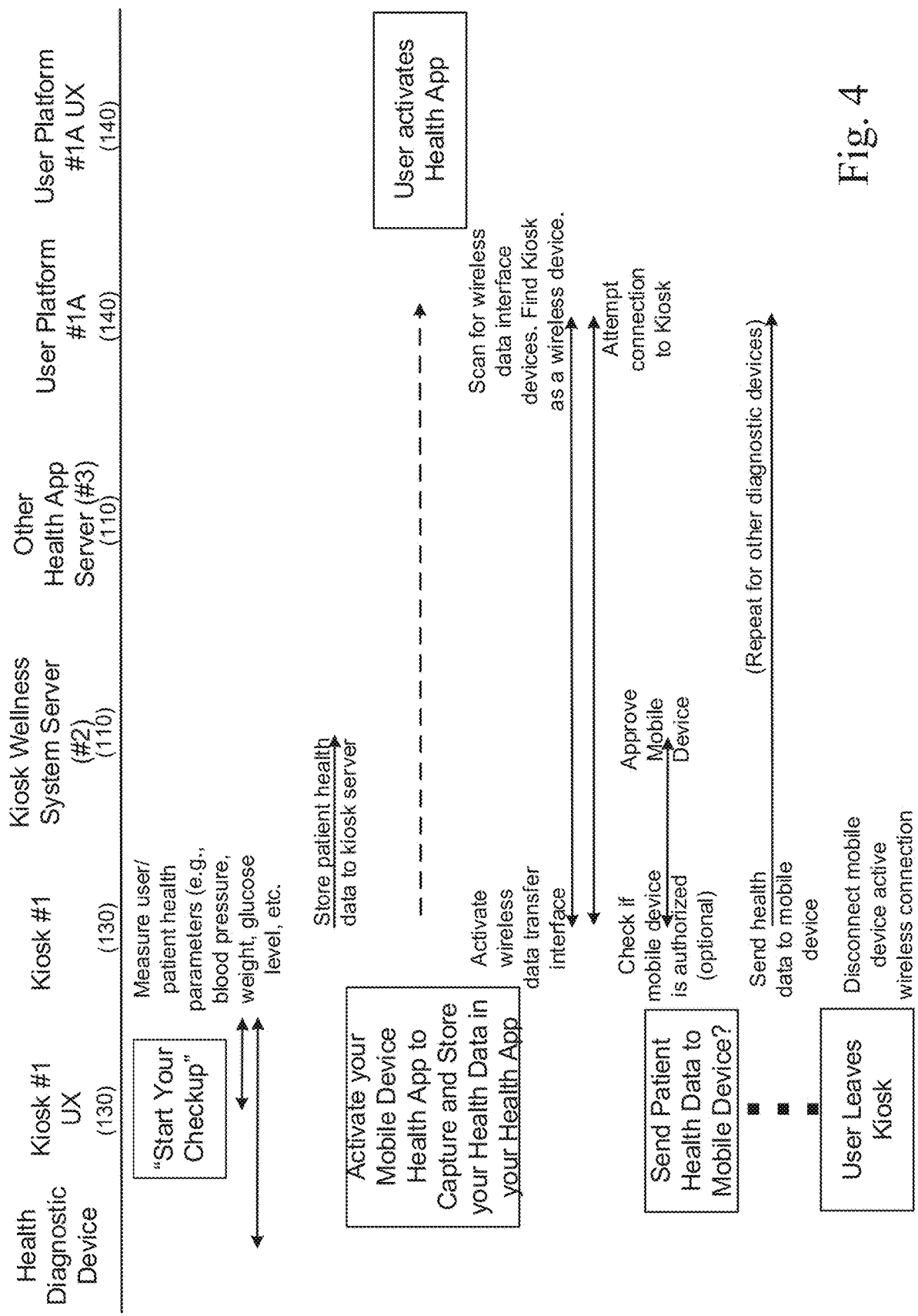
FIG. 4 illustrates an operational sequence diagram showing an example of a user device at a user platform interacting with a kiosk and health diagnostic devices according to an example embodiment of a method as described herein.

FIG. 4 illustrates an operational sequence diagram showing an example of a user device at a user platform interacting with a kiosk and health diagnostic devices according to an example embodiment of a method as described herein. Referring to FIG. 4, upon completion of the installation of the mobile device health data transfer app 1407 on the user's mobile device 140, the user can position themselves in front of a particular kiosk 130. As described above, the user can perform a login operation at the kiosk 130 and pair their mobile device 140 with the kiosk 130. In other embodiments, the pairing operation is not required. The user can also authenticate with the kiosk 130 as described above. Upon completion of the kiosk 130 login and authentication operations, the kiosk health data transfer application (app) 1307 can use the user interface of kiosk 130 to prompt the user to "Start a Health Checkup" as shown in FIG. 4. Using medical diagnostic devices attached or interfaced with the kiosk 130, the user can use the medical diagnostic devices to obtain or produce health data related to the user/patient. As described above, this health data can include the user/patient's blood pressure, heart rate, weight, oxygen saturation level devices, glucose level, and/or the like. This user/patient health data can be initially retained by the kiosk 130. Additionally, the user/patient health data can be transferred to the kiosk wellness system server 110 or other network cloud location via network 115.

Referring still to FIG. 4, the user can also initiate functionality in the kiosk health data transfer app 1307 to cause the kiosk 130 to send the user/patient health data to the user's mobile device 140. As part of this process, the kiosk health data transfer app 1307 can use the user interface of kiosk 130 to prompt the user to "Activate your Mobile Device Health App to Capture and Store your Health Data in your Health App" as shown in FIG. 4. The user can launch or activate their Health App on their mobile device 140. The activation of their Health App on their mobile device 140 initiates the functionality of the mobile device health data transfer app 1407.

Once the kiosk health data transfer app 1307 is activated at the kiosk 130 and the Health App or mobile device health data transfer app 1407 is activated on the user's mobile device 140, the kiosk 140 can activate its wireless data transfer interface and advertise its availability for connection using one or more of the proxies added for the medical diagnostic devices as described above. Concurrently, the mobile device 140 can use its wireless data transfer interface to begin scanning for available data connections. In one example embodiment, the kiosk 140 can use a standard Bluetooth™ Low Energy (BTLE) protocol to initiate the wireless data connection. Similarly, the kiosk 140 can advertise as or with a BTLE profile proxy, which can be recognized and used by the Health App on the mobile device 140 to wirelessly receive the user/patient health data from the medical diagnostic device of the kiosk 140. In some cases, standard fitness tracking apps can use the BTLE profile to wirelessly transfer the user/patient health data to the user's mobile device 140. The kiosk 130 can translate from the health diagnostic device's internal proprietary application programming interface (API) to a standard profile API to provide data to the application requesting the data on the mobile device 140.

In the example embodiment, the kiosk 140 can also perform processing operations to ensure that a wireless data connection is established between the kiosk 130 and the correct (authorized) mobile device 140. As part of these processing operations, the kiosk 130 can use its wireless data transfer interface to advertise that the kiosk 140 is a proxy for the health diagnostic device from which health data is sought. The wireless data transfer interface of the mobile device 140 can recognize this health diagnostic device proxy invitation and begin a data connection with the kiosk 140. The kiosk 140 can use its user interface to display a pop-up message on the kiosk 140 prompting the user to confirm the data connection with the mobile device 140. An identifier of the mobile device 140 (e.g., a phone number or name) can be used to identify the correct mobile device 140. The user can provide an input at the kiosk 130 to confirm the data connection with the mobile device 140. The data connection can be completed and the user/patient's health data can be wirelessly transferred from the health diagnostic device via the kiosk 130 to the user's mobile device 140.

Referring still to FIG. 4, the wireless transfer of the user/patient's health data to the mobile device 140 can be repeated for each of the health diagnostic devices attached or interfaced with the kiosk 130. Thus, the user can wirelessly transfer the user's health data from any of the kiosk 130 medical diagnostic devices to the user's mobile device or network cloud storage. When the user has completed the desired data transfers, the user can simply leave the proximity of the kiosk 130. The departure of the user's mobile device from the proximity of the kiosk 130 will cause the wireless data connection to disconnect. Upon detection of the wireless data disconnection, the kiosk 130 can logout the user and erase the user's health data from the kiosk 130. The wireless data connection with the user's mobile device can also be terminated to ensure the security of the user's data. Thus, the user can conveniently and securely establish a wireless data connection between a kiosk 130 medical diagnostic device and the user's mobile device to wirelessly transfer the user's health data from the kiosk 130 to the user's mobile device 140 and/or network cloud storage.

Figure 5:
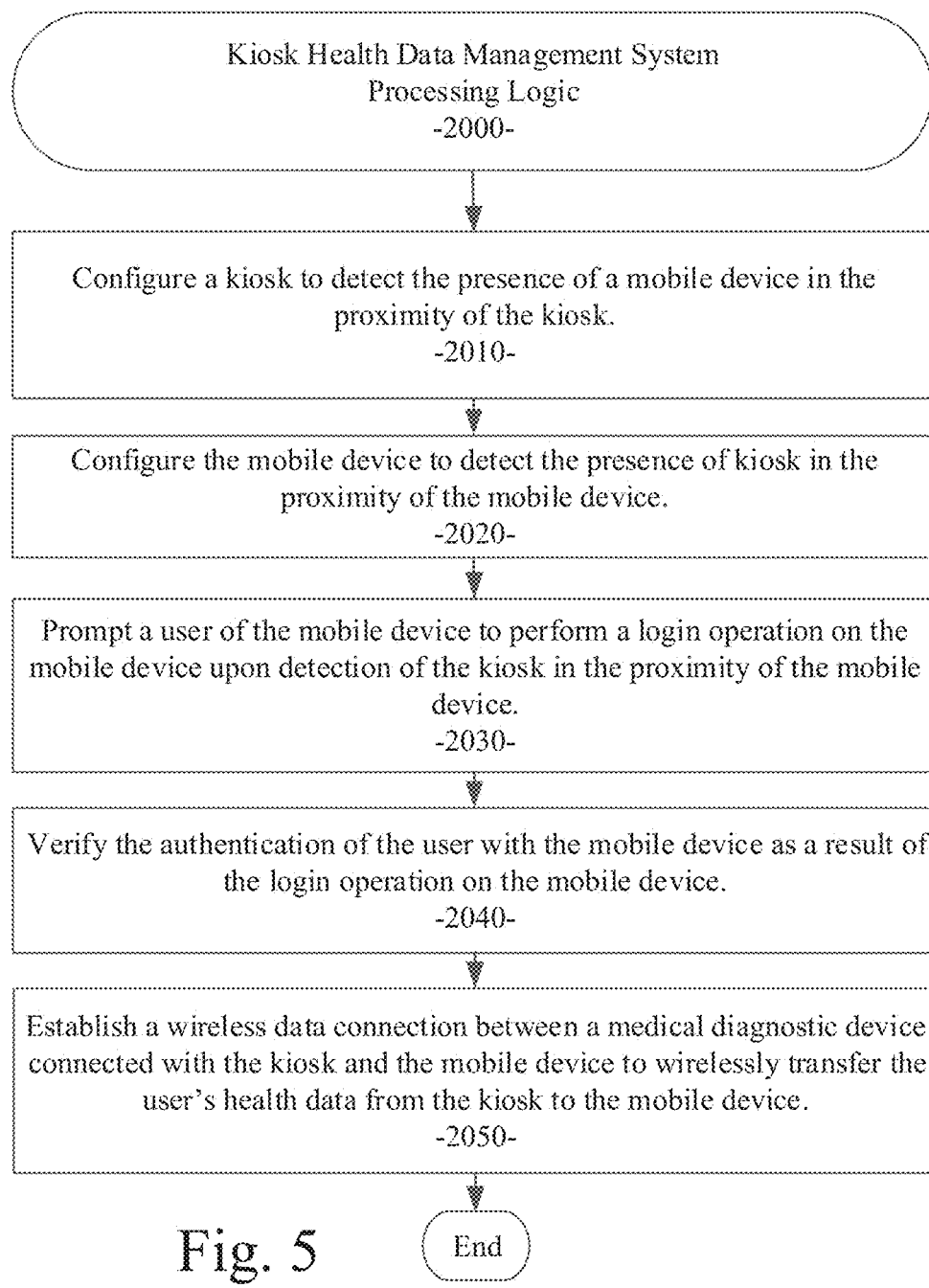
FIG. 5 illustrates a processing flow diagram that illustrates an example embodiment of a method as described herein.

Referring now to FIG. 5, a processing flow diagram illustrates an example embodiment of a method implemented as described herein. The method 2000 of an example embodiment includes: configuring a kiosk to detect the presence of a mobile device in the proximity of the kiosk (processing block 2010); configuring the mobile device to detect the presence of kiosk in the proximity of the mobile device (processing block 2020); prompting a user of the mobile device to perform a login operation on the mobile device upon detection of the kiosk in the proximity of the mobile device (processing block 2030); verifying the authentication of the user with the mobile device as a result of the login operation on the mobile device (processing block 2040); and establishing a wireless data connection between a medical diagnostic device connected with the kiosk and the mobile device to wirelessly transfer the user's health data from the kiosk to the mobile device (processing block 2050).

Figure 6:
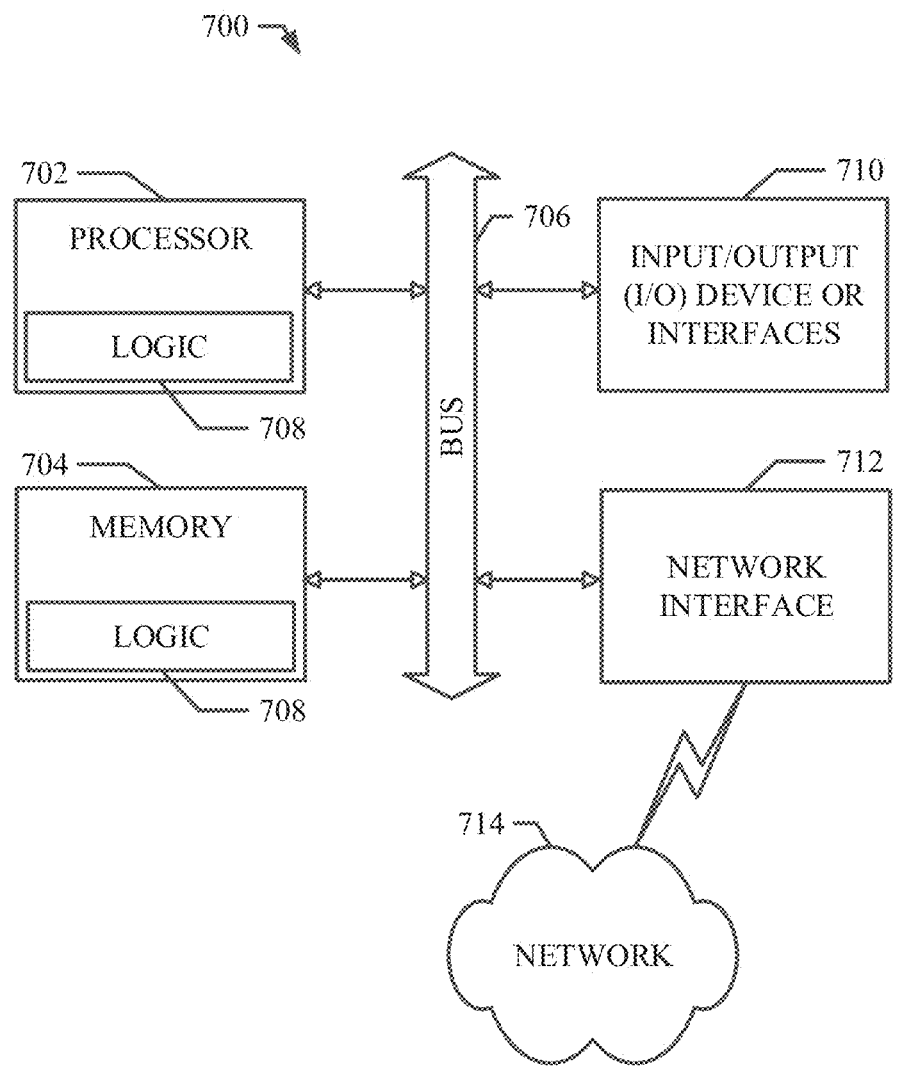
FIG. 6 shows a diagrammatic representation of a machine in the example form of a computer system within which a set of instructions when executed may cause the machine to perform any one or more of the methodologies discussed herein.

FIG. 6 shows a diagrammatic representation of a machine in the example form of a mobile computing and/or communication system 700 within which a set of instructions when executed and/or processing logic when activated may cause the machine to perform any one or more of the methodologies described and/or claimed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a laptop computer, a tablet computing system, a Personal Digital Assistant (PDA), a cellular telephone, a smartphone, a mobile device, a web appliance, a network router, switch or bridge, or any machine capable of executing a set of instructions (sequential or otherwise) or activating processing logic that specify actions to be taken by that machine. Further, while only a single machine is illustrated, the term "machine" can also be taken to include any collection of machines that individually or jointly execute a set (or multiple sets) of instructions or processing logic to perform any one or more of the methodologies described and/or claimed herein.

The example mobile computing and/or communication system 700 includes a data processor 702 (e.g., a System-on-a-Chip (SoC), general processing core, graphics core, and optionally other processing logic) and a memory 704, which can communicate with each other via a bus or other data transfer system 706. The mobile computing and/or communication system 700 may further include various input/output (I/O) devices and/or interfaces 710, such as a touchscreen display and optionally a network interface 712. In an example embodiment, the network interface 712 can include one or more radio transceivers configured for compatibility with any one or more standard wireless and/or cellular protocols or access technologies (e.g., 2nd (2G), 2.5, 3rd (3G), 4th (4G) generation, and future generation radio access for cellular systems, Global System for Mobile communication (GSM), General Packet Radio Services (GPRS), Enhanced Data GSM Environment (EDGE), Wideband Code Division Multiple Access (WCDMA), LTE, CDMA2000, WLAN, Wireless Router (WR) mesh, and the like). Network interface 712 may also be configured for use with various other wired and/or wireless communication protocols, including TCP/IP, UDP, SIP, SMS, RTP, WAP, CDMA, TDMA, UMTS, UWB, WiFi, WiMax, Bluetooth™, IEEE 802.11x, and the like. In essence, network interface 712 may include or support virtually any wired and/or wireless communication mechanisms by which information may travel between the mobile computing and/or communication system 700 and another computing or communication system via network 714.

The memory 704 can represent a machine-readable medium on which is stored one or more sets of instructions, software, firmware, or other processing logic (e.g., logic 708) embodying any one or more of the methodologies or functions described and/or claimed herein. The logic 708, or a portion thereof, may also reside, completely or at least partially within the processor 702 during execution thereof by the mobile computing and/or communication system 700. As such, the memory 704 and the processor 702 may also constitute machine-readable media. The logic 708, or a portion thereof, may also be configured as processing logic or logic, at least a portion of which is partially implemented in hardware. The logic 708, or a portion thereof, may further be transmitted or received over a network 714 via the network interface 712. While the machine-readable medium of an example embodiment can be a single medium, the term "machine-readable medium" should be taken to include a single non-transitory medium or multiple non-transitory media (e.g., a centralized or distributed database, and/or associated caches and computing systems) that stores the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

As described herein for various example embodiments, a system and method to enable a kiosk to aggregate wireless devices and report health information to a mobile consumer device are disclosed. In the various example embodiments described herein, a computer-implemented tool or software application (app) as part of a user data transfer system in a network ecosystem is described to automate and improve the authentication and verification of parties in a kiosk transaction. As such, the various embodiments as described herein are necessarily rooted in computer and network technology and serve to improve these technologies when applied in the manner as presently claimed. In particular, the various embodiments described herein improve the use of mobile device technology and data network technology in the context of kiosk transactions via electronic means.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for wirelessly transferring user health information from a medical diagnostic device connected with a kiosk to a mobile device, the method comprising: configuring a kiosk to detect the presence of a mobile device of a user in the proximity of the kiosk, the kiosk further configured to facilitate the collection and transfer of user health information from the kiosk after the user is logged in at the kiosk; configuring the mobile device to detect the presence of kiosk in the proximity of the mobile device; prompting a user of the mobile device to perform a login operation on the mobile device upon detection of the kiosk in the proximity of the mobile device; verifying the authentication of the user with the mobile device as a result of the login operation on the mobile device; transferring kiosk session keys from the mobile device to the kiosk in proximity of the mobile device upon authentication of the user with the mobile device;

initiating a login operation in a different session on the kiosk using the kiosk session keys transferred from the mobile device without requiring the user to perform a separate login operation or authentication process on the kiosk in the different session;

establishing a wireless data connection between a medical diagnostic device connected with the kiosk and the mobile device upon a successful login operation on the kiosk; and initiating a transfer of user health information from the medical diagnostic device connected with the kiosk to the mobile device via the wireless data connection.

2. The method of claim 1 further including using a wireless data communication technology to detect the presence of kiosk, the wireless data communication technology being of a type from the group consisting of: Bluetooth™ (BT) and Near-field Communication (NFC).

3. The method of claim 1 wherein the kiosk is configured to include a wide area data network interface.

4. The method of claim 1 wherein the kiosk is configured to include a wide area data network interface and the kiosk is configured to communicate with a kiosk health data management system via the wide area data network interface.

5. The method of claim 1 further including configuring the kiosk and the mobile device to exchange user information and device configuration information upon detection of the kiosk in the proximity of the user mobile device.

6. The method of claim 5 wherein the user information and device configuration information includes a user identity, a mobile device identifier, a kiosk identifier, a kiosk geographical location, a kiosk type code, and a kiosk configuration.

7. The method of claim 1 further including configuring the kiosk to register with a kiosk health data management system via the wide area data network interface.

8. The method of claim 1 further including configuring the mobile device to register with a kiosk health data management system via the wide area data network interface.

9. The method of claim 1 further including causing the kiosk to advertise on a wireless data interface a proxy profile of a medical diagnostic device in data communication with the kiosk.

10. A system for wirelessly transferring user health information from a medical diagnostic device connected with a kiosk to a mobile device, the system comprising: a kiosk having a first data processor and a wireless network interface, in data communication with the first data processor, for communication on a wireless data network, the kiosk further including a wide area data network interface for communication on a wide area data network, the kiosk further including a medical diagnostic device connected with the kiosk; a mobile device having a second data processor and a wireless network interface, in data communication with the second data processor, for communication on the wireless data network, the mobile device further including a wide area data network interface for communication on the wide area data network; and the kiosk being configured to detect the presence of the mobile device of a user in the proximity of the kiosk, the kiosk further configured to facilitate the collection and transfer of user health information from the kiosk after the user is logged in at the kiosk, the mobile device being configured to detect the presence of the kiosk in the proximity of the mobile device, the mobile device being configured to prompt a user of the mobile device to perform a login operation on the mobile device upon detection of the kiosk in the proximity of the user mobile device, the mobile device being configured to verify the authentication of the user with the mobile device as a result of the login operation on the mobile device, the system being further configured to transfer kiosk session keys from the mobile device to the kiosk in proximity of the mobile device upon authentication of the user with the mobile device, the system being further configured to initiate a login operation in a different session on the kiosk using the kiosk session keys transferred from the mobile device without requiring the user to perform a separate login operation or authentication process on the kiosk in the different session, system being further configured to establish a wireless data connection between the medical diagnostic device connected with the kiosk and the mobile device upon a successful login operation on the kiosk; and the system being further configured to initiate a transfer of user health information from the medical diagnostic device connected with the kiosk to the mobile device via the wireless data connection.

11. The system of claim 10 being configured to use a wireless data communication technology to detect the presence of kiosk, the wireless data communication technology being of a type from the group consisting of: Bluetooth™ (BT) and Near-field Communication (NFC).

12. The system of claim 10 wherein the kiosk is configured to include a wide area data network interface.

13. The system of claim 10 wherein the kiosk is configured to include a wide area data network interface and the kiosk is configured to communicate with a kiosk health data management system via the wide area data network interface.

14. The system of claim 10 being configured to cause the kiosk and the mobile device to exchange user information and device configuration information upon detection of the kiosk in the proximity of the user mobile device.

15. The system of claim 14 wherein the user information and device configuration information includes a user identity, a mobile device identifier, a kiosk identifier, a kiosk geographical location, a kiosk type code, and a kiosk configuration.

16. The system of claim 10 being configured to cause the kiosk to register with a kiosk health data management system via the wide area data network interface.

17. The system of claim 10 being configured to cause the mobile device to register with a kiosk health data management system via the wide area data network interface.

18. The system of claim 10 being configured to cause the kiosk to advertise on a wireless data interface a proxy profile of a medical diagnostic device in data communication with the kiosk.

19. A non-transitory machine-useable storage medium embodying instructions which, when executed by a machine, cause the machine to:

configure a kiosk to detect the presence of a mobile device of a user in the proximity of the kiosk, the kiosk further configured to facilitate the collection and transfer of user health information from the kiosk after the user is logged in at the kiosk;

configure the mobile device to detect the presence of kiosk in the proximity of the mobile device; prompt a user of the mobile device to perform a login operation on the mobile device upon detection of the kiosk in the proximity of the mobile device;

verify the authentication of the user with the mobile device as a result of the login operation on the mobile device; transfer kiosk session keys from the mobile device to the kiosk in proximity of the mobile device upon authentication of the user with the mobile device;

initiate a login operation in a different session on the kiosk using the kiosk session keys transferred from the mobile device without requiring the user to perform a separate login operation or authentication process on the kiosk in the different session; establish a wireless data connection between a medical diagnostic device connected with the kiosk and the mobile device upon a successful login operation on the kiosk; and initiating a transfer of user health information from the medical diagnostic device connected with the kiosk to the mobile device via the wireless data connection.

20. The non-transitory machine-useable storage medium of claim 19 being further configured to use a wireless data communication technology to detect the presence of kiosk, the wireless data communication technology being of a type from the group consisting of: Bluetooth™ (BT) and Near-field Communication (NFC).

* * * * *